United States Patent [19]

Kawamoto et al.

[11] 4,261,202
[45] Apr. 14, 1981

[54] APPARATUS FOR DETERMINING CARBON CONTENTS IN MOLTEN METAL

[75] Inventors: Taizo Kawamoto, Osaka; Hiroyuki Nakashima, Kisarazu; Yozo Takemura, Chita; Kaname Ohno, Kyoto, all of Japan

[73] Assignees: Kawaso Electric Industrial Co., Ltd., Osaka; Nippon Steel Corporation, Tokyo, both of Japan

[21] Appl. No.: 71,054

[22] Filed: Aug. 30, 1979

[30] Foreign Application Priority Data

Jul. 9, 1978 [JP] Japan ............................. 53-110490

[51] Int. Cl.$^3$ ............................................ G01N 25/06
[52] U.S. Cl. ................................... 73/354; 73/17 R
[58] Field of Search ............... 73/354, 17 R, DIG. 9

[56] References Cited

U.S. PATENT DOCUMENTS

| | | | |
|---|---|---|---|
| 3,559,452 | 2/1971 | Prebix et al. | 73/17 R |
| 3,685,359 | 8/1972 | Boron et al. | 73/354 |
| 3,709,040 | 1/1973 | Coe | 73/354 |
| 3,748,908 | 7/1973 | Falk | 73/354 |

Primary Examiner—Gerald Goldberg
Assistant Examiner—Joseph W. Roskos
Attorney, Agent, or Firm—Burgess, Ryan and Wayne

[57] ABSTRACT

An apparatus for determining carbon contents in molten metal comprising an entrance chamber with an entry port in a side wall, a sampling chamber, a ring-shaped disk to be set between both chambers and a temperature sensing means which is protected from the flowing sample metal by a protective thermal insulation member, protruding through the entrance chamber to the sampling chamber. The molten metal flowing from the entry port is cooled by contacting with the protective thermal insulation member. The insulation member will turn to be a riser when the sample metal starts solidifying in the sampling chamber. Thus enabling precise rapid carbon determination and simultaneously offering appropriate specimen for spectrographic analysis.

14 Claims, 13 Drawing Figures

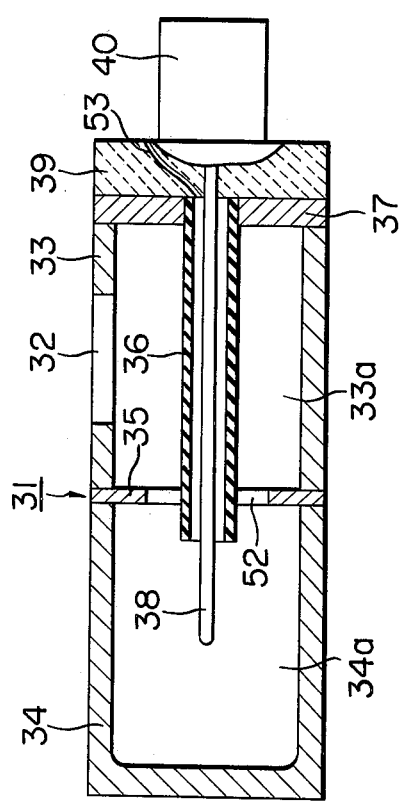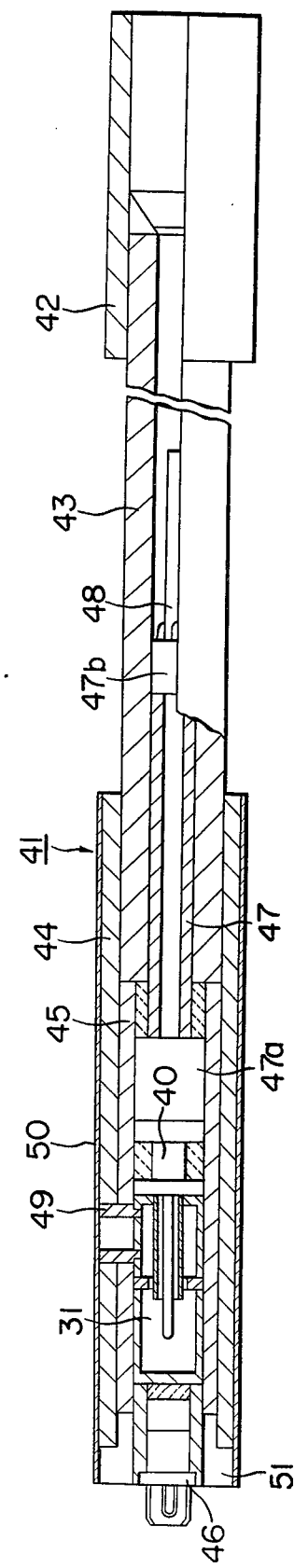

APPARATUS FOR DETERMINING CARBON CONTENTS IN MOLTEN METAL

BACKGROUND OF THE INVENTION

The present invention relates to an apparatus for determining the carbon contents of molten metal and simultaneously accomplishing an effective sampling of molten metal and a measurement of a molten metal bath temperature.

There have been invented and used a variety of carbon determinators which may be directly placed in a molten metal bath for quick determination of the carbon contents thereof. An entry port of the carbon determinator is, in common case, provided in the upper portion of the container side-wall. A thermocouple measuring phase change temperature of the molten metal is set in the upper portion or the lower portion of the container, and consists of platinum platinum-rhodium wire insulated in a U-shaped quartz tube.

In such a carbon determinator with the thermocouple protruded from the bottom of the container, when the molten metal is sampled by the carbon determinator a shrinkage cavity is occasionally left adjacent to the entry port of the container and the form of the thermocouple is left in the bottom of the sample. Therefore, the portion of the sample which may be used as a specimen for spectrographic analysis will be quite limited. In the worst case, the shrinkage cavity adjacent to the entry port will be communicated with the cavity formed by the air contained in the quartz tube of the thermocouple. As a result, a cavity is formed in the center part of the sample, so that a reliable specimen for spectrographic analysis is not available.

In the carbon determinator in which the thermocouple is protruded from the upper portion of the container, since the molten metal sampling chamber is provided in the lower part of the container, even if the shrink cavity is formed in the adjacent portion of the entry port, the molten metal taken in the bottom of the container is sufficiently used for the spectrographic analysis. But, since the thermocouple is placed adjacent to the entry port, there exists the defect that the thermocouple is bent by the force of molten metal flowing into the container. The carbon contents of the molten metal is measured by the phase change temperature, but the correct measurement of the carbon contents is executed only when the thermocouple is set in the center of the container. In case the thermocouple is bent, the carbon contents should not be measured correctly and whether the carbon contents measured by such a faulty carbon determinator is correct or not is ascertained only after the molten metal is analyzed by other means. Thus, the reliability of the carbon determination performed by such means will not be accountable for the precise quality control in the metal industry.

SUMMARY OF THE INVENTION

Accordingly one of the object of the present invention is to provide a proper apparatus for determining the carbon contents in a molten metal wherein the sufficient quantity of the molten metal is sampled and measured its temperature, as it solidifies, for determining the carbon contents.

Another object of the present invention is to provide an apparatus for determining the carbon contents in molten metal wherein the molten metal is cooled and inducted into the sampling chamber and the molten metal in the entrance chamber to be stayed in liquid condition, as the sample in the sampling chamber being solidified.

The above and other objects, effects and features of the present invention will become more apparent from the following description of some preferred embodiments thereof taken in conjunction with the accompanying drawings.

BRIEF DESCRIPTION OF THE DRAWINGS

FIG. 6 is a longitudinal sectional view of a first embodiment of a sampling unit in accordance with the present invention;

FIG. 7 is a longitudinal sectional view of a sampling lance incorporating the sampling unit shown in FIG. 6;

Same reference numerals are used to designate similar parts throughout the figures.

DESCRIPTION OF THE PREFERRED EMBODIMENTS

Prior Art, FIG. 1 through FIG. 5

Figure 1:
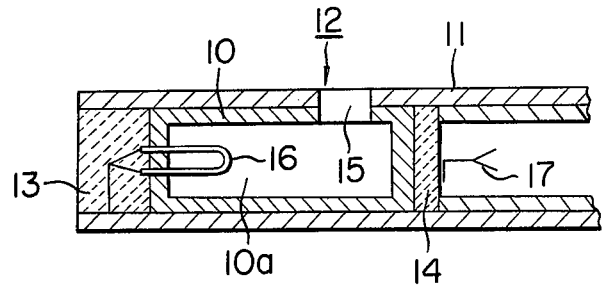
FIG. 1 is a longitudinal sectional view of a prior art sampling unit.

Prior to the description of the preferred embodiments of the present invention, some carbon determinators in the prior art will be described. FIG. 1 shows an outline of a known carbon determinator. In FIG. 1, a container 10 is fixed in the bottom of the probe 12 of a cardboard tube 11 by refractory cements 13 and 14. An entry port 15 is provided in the upper portion of the container 10 by perforating the cardboard tube 11 and a thermocouple 16 is provided in the bottom of the container 10 and is connected to an outer temperature measuring apparatus (not shown) through a thermal barrier 17 and lead wires.

Figure 2:
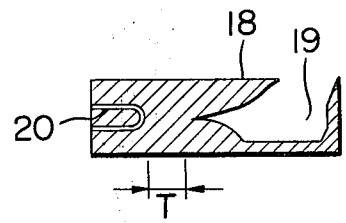
FIG. 2 is a longitudinal sectional view of a sample obtained by the sampling unit shown in FIG. 1.

When the measuring probe 12 attached to the top of a supporting means (not shown) is inserted into a molten metal bath, the molten metal enters the container 10. Since deoxidizer, such as aluminum, is usually contained in the container, the molten metal flowing into the container 10 will be calmed or "Killed" and filled in the bottom of the container 10. Also, the solidification of molten metal is promoted. However, when the probe, in the prior art is taken out of the molten metal bath, the molten metal in the portion adjacent to the entry port runs out from the container and the specimen 18 solidified in the container 10 forms a cavity 19 in the portion adjacent to the entry port as shown in FIG. 2. Also, the form 20 of the thermocouple 16 is left in the bottom of the container 10, the portion to be used as a specimen for the spectrographic analysis is T; thus, there is the defect that this portion is very small.

At the same time, another defect is also anticipated that the air left in the quartz thermocouple insulator tube will be extremely expanded by the heat of the flowing molten metal and will occasionally break the tube and permeate into a solidifying sample. This sometimes forms a little cavity in the sample, above the thermocouple, and the cavity will be easily connected to the shrinkage cavity 19. Therefore, the solidified metal in the container 10 could not be used as a specimen for spectrographic analysis.

Figure 3:
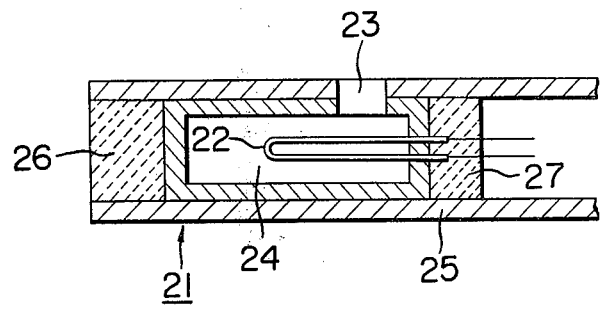
FIG. 3 is a longitudinal sectional view of another prior art sampling unit.
Figure 4:
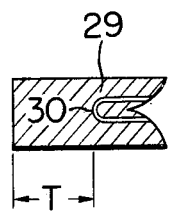
FIG. 4 and FIG. 5 are longitudinal sectional views, respectively, of samples obtained by the sampling unit shown in FIG. 3.
Figure 5:
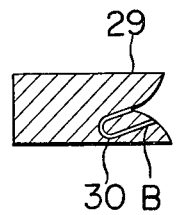

In a measuring probe 21 as shown in FIG. 3, a thermocouple 22 and an entry port 23 are provided in the upper portion of the container 24 which is fixed in the bottom of a cardboard tube 25 by refractory cements 26 and 27. As shown in FIG. 4, in the specimen 29 sampled in the container 24, the portion to be used for a specimen of the spectrographic analysis is large enough. However, when inspecting the specimen 29 in later stage there is a case where the form 30 of the thermocouple 22 is left in bent state. In such case, carbon contents determined from the thermal arrest temperature, measured by the deformed faulty thermocouple will be far from true value and accordingly given information will be totally unreliable.

The Invention, First Embodiment, FIGS. 6 and 7

On referring to FIG. 6, a body structure 31 in a first embodiment of the present invention is shown. This body structure 31 comprising an entrance chamber 33a, defined by a cylindrical wall structure 33 having a entry port 32 in its side wall, a sampling container 34 which defines a sampling chamber 34a and a ring-shaped disk 35 is placed between one end of cylindrical wall structure 33 and the container 34. A cover plate 37 in which a protective thermal insulation tube 36 is fixed is attached in the other end of the cylindrical wall structure 33. A temperature sensing unit 40 having a temperature sensor 38 supported by an insulator flange 39 is attached in the outer portion of the cover plate 37 and the temperature sensor 38 is extended through the protective thermal insulation tube 36 in the sampling container 34. The temperature sensor 38 preferably consists of a platinum platinum-rhodium thermocouple is insulated in a quartz tube.

The body structure 31 is incorporated in a sampling lance 41 as shown in FIG. 7. The sampling lance 41 comprises a guide tube 42 having the function of a acceptance guide when the sampling lance 41 is connected to a supporting means (not shown), an intermediate tube 43 which is also made of the long cardboard tube and has its one end inserted into the guide tube 42, an outer tube 44 which is also made of cardboard and fitted over the other end of the intermediate tube 43, a thermal insulating member 45 which is led in the outer tube 44, the body structure 31 is surrounded by the thermal insulating member 45 and a metal bath temperature sensor 46 outwardly extended from the lance 41. One end of a connector supporting tube 47 which is extended through the intermediate tube 43 is communicated with the temperature sensing unit 40 of the body structure 31 and the other end of the connector supporting tube 47 is communicated with a connector member 48 which is plugged in to a receptacle of the supporting means (not shown).

An entry port guide 49 is radially extended in the entry port 32 of the body structure 31 through the side wall of the outer tube 44 and a thermal insulating member 45 and a covering 50 closing the open end of the entry port guide 49 is surrounding the outer surface of the outer tube 44. The covering 50 can prevent the slag from entering the body structure when the sampling lance 41 is inserted into the molten metal bath, but is adapted to be fractured when brought in contact with molten metal so that molten metal may flow into the body structure. The covering 50 is made of a paper. The top covering 51 is substantially used for supporting the metal bath temperature sensor 46.

Next the mode of the operation of the sampling lance with the above construction will be described. When the sampling lance 41 is inserted into the molten metal bath, the covering 50 is not fractured by the slag, but is fractured by the molten metal as described above. Thus, when the covering 50 is fractured, the molten metal flows into the entrance chamber 33a through the entry port guide 49 and the entry port 32. Since the deoxidizer (not shown) is previously charged in the entrance chamber 33a, the molten metal is "Killed" and taken in the entrance chamber 33a. There, since the molten metal impinges against the thermal insulation tube 36, the heat of the molten metal is absorbed by the protective thermal insulation tube 36. Thus, the cooled molten metal flows through the passage 52 between the ring-shaped disk 35 and the protective thermal insulation tube 36 into the sampling chamber 34a. When the molten metal flows into the entrance chamber 33, the temperature sensor 38 is protected by the protective thermal insulation tube 36. Since almost all the air in the chambers 33a and 34a is discharged through the entry port, and the air left in the insulation tube 36 is vented off through an air passage 53, the molten metal is completely filled in the sampling chamber 34a. The molten metal filled in the chamber 34a, whose heat is taken off by the sampling container 34, progressively proceeds its solidification, but, since the protective thermal insulation tube 36 has a heat holding function, as a riser, so that the temperature of the molten metal in the entrance chamber 33a is maintained somewhat for the required period by means of the protective thermal insulation tube 36. Therefore, the solidification of the molten metal in the sampling chamber 34a progressively proceeds from the bottom portion of the sampling chamber 34a towards the entrance chamber 33a and the solidification of the molten metal progressively proceeds, but, since the molten metal in the entrance chamber 33a is not solidified by the temperature holding function of the thermal insulation tube, the molten metal in the entrance chamber 33a is put into the sampling chamber 34a. Thus, any shrinkage cavities will not be formed in the metal sample in the sampling chamber 34a. Even when shrinkage cavities are found in the metal sample around the entrance chamber 33a, they will not be extend into the metal sample in the sampling chamber 34a.

The carbon contents of the metal sample in the sampling chamber 34a is determined by temperature change corresponding to the lapse of the solidification which is detected by the temperature sensor. The protective thermal insulation tube 36 is preferably made of the refractory materials such as quartz, ceramic or metals which can withstand the molten metal.

Figure 8:
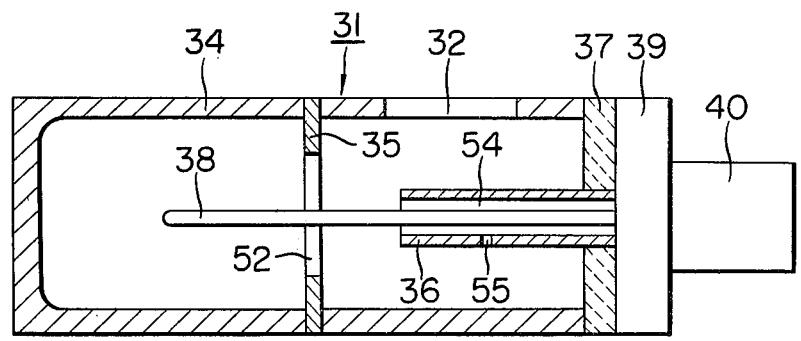
FIGS. 8 and 9 are longitudinal sectional views, respectively, of a first and a second modifications of the first embodiment shown in FIG. 6.

Second Embodiment, FIG. 8

In FIG. 8 is shown a second embodiment of the body structure 31 shown in FIG. 6. This modification is substantially similar in construction to the first embodiment except that the protective thermal insulation tube 36 is formed shorter than that in FIG. 6 and covers the temperature sensor 38 so that it may be prevented from being directly hit by the molten metal flowing through the entry port 32 into the entrance chamber 33a. In addition, a lateral hole 55 is formed through the side wall of the protective thermal insulation tube 36 so as to communicate between the inside room 54 of the protective thermal insulation tube 36 and the entrance chamber 33a.

The effects and features of the second embodiment are substantially similar to those of the first embodiment described above.

Figure 9:
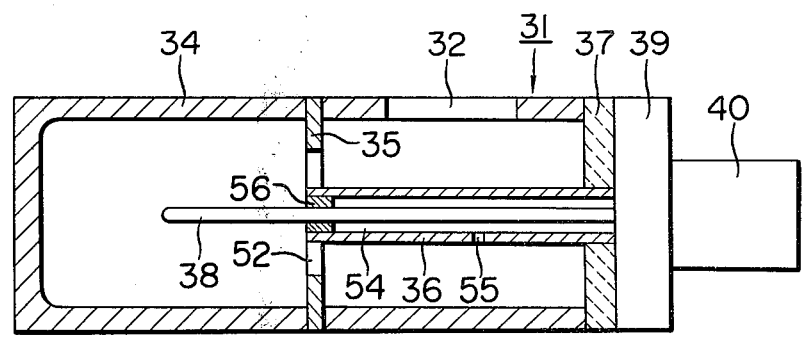

Third Embodiment, FIG. 9

A third embodiment shown in FIG. 9 is also substantially similar in construction to the first embodiment shown in FIG. 6 except that the open end of the protective thermal insulation tube 36 is closed with a plug 57 and the lateral hole 55 are formed through the side wall of the protective thermal insulation tube 36 so that air in the inside room 54 may be discharged into the entrance chamber 33a.

The third embodiment is also substantially similar in effects and features to the first embodiment.

Figure 10:
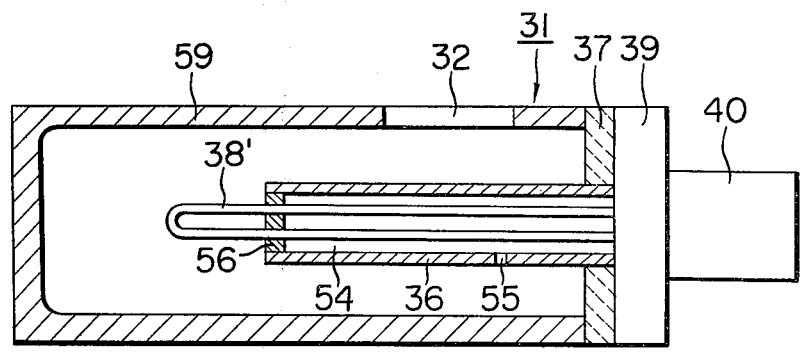
FIG. 10 is a longitudinal sectional view of a second embodiment of a sampling unit in accordance with the present invention.

Fourth Embodiment, FIG. 10

A fourth embodiment shown in FIG. 10 is substantially similar in construction to the first embodiment shown in FIG. 6 except that a container 57 is not provided any ring-shaped disk for dividing the body structure 31 in two chambers. The temperature sensor 38 is formed by a U-shaped quartz tube into which a platinum platinum-chodium thermocouple is inserted and is covered by the thermal insulation tube 36 which is limited to a length that the molten metal does not directly impinge to the temperature sensor. The open end of the protective thermal insulation tube 36 is closed with a plug 56.

The fourth embodiment is also substantially similar in function for protecting from the impingement of the molten metal to the first embodiment. The temperature sensing capability of the U-shaped temperature sensor 38' is same as that of the straight temperature sensor 38.

Figure 11:
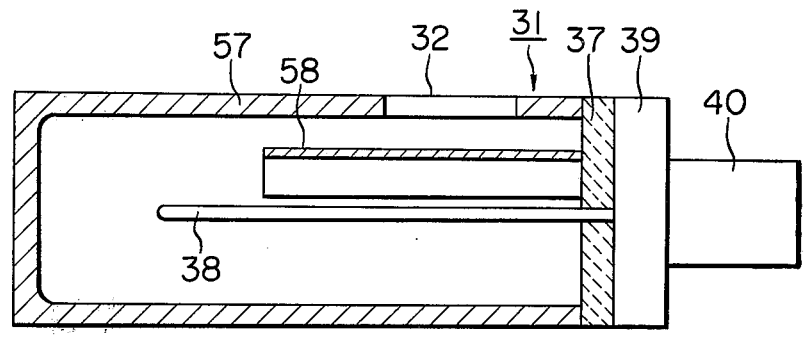
FIG. 11 is a longitudinal sectional view of a modification thereof.
Figure 12:
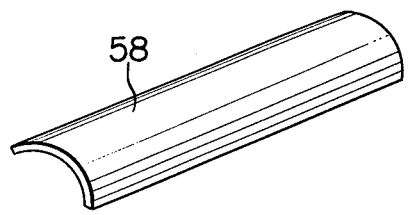
FIG. 12 is a perspective view of a protective cover or wall thereof.

Fifth Embodiment, FIGS. 11 and 12

The fifth embodiment shown in FIG. 11 is substantially similar in construction to the fourth embodiment shown in FIG. 10 except that instead of the protective thermal insulation tube 36, the temperature sensor 38 is guarded by a protective thermal insulation wall 58 arcuate in cross section as shown in FIG. 12. The protective thermal insulation wall 58 is as effective as the protective thermal insulation tube 36 in preventing the direct impingement of the molten metal flowing through the entry port 32 to the temperature sensor 38.

Figure 13:
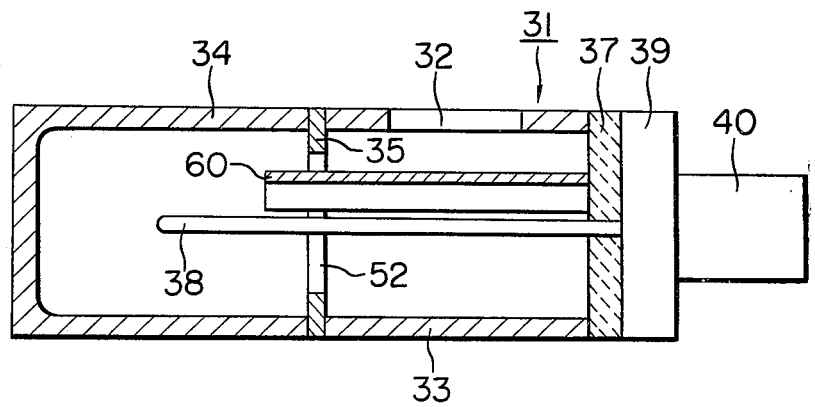
FIG. 13 is a longitudinal sectional view of another embodiment of a sampling unit in accordance with the present invention.

Sixth Embodiment, FIG. 13

The sixth embodiment shown in FIG. 13 is substantially similar in construction to the first embodiment shown in FIG. 6 except that instead of the protective thermal insulation tube 36, the temperature sensor 38 is guarded by a protective thermal insulation wall 58.

The sixth embodiment is also substantially similar in effects and features to the first embodiment.

The effects, features and advantages of the present invention may be summarized as follows:

(1) Since the entry port is formed in the side wall of the body structure and the temperature sensor is protruded to the sampling chamber, from the inside wall of the body structure in the contrary direction to the insertion of the sampling lance, the specimen used for the spectrographic analysis is not influenced by the shrinkage cavity and the metal between the bottom wall of the body structure and the top portion of the temperature sensor is satisfactorily used as a specimen.

(2) Since the entry port is formed in the side wall of the body structure and the temperature sensor is protruded to the sampling chamber, any process for attaching the temperature sensor in the bottom of the sampling container is not required. Therefore, the metal solidified as a specimen is sampled in the same condition.

(3) In the above construction, since the thermal insulation tube or wall is provided between the temperature sensor and the entry port and the flowing molten metal does not directly impinge to the temperature sensor, the defect of the strength of the temperature sensor is substantially improved.

(4) In the above construction, since the thermal insulation tube or wall having a thermal insulating portion between the temperature sensor and the entry port is protrusively provided in the body structure, and the flowing molten metal once impinges to the thermal insulation tube or wall and then flows into the sampling chamber, in the case of determining the carbon content of the molten steel in a temperature high than the prior art, the measuring time is shortened because the molten metal is cooled by the thermal insulation tube or wall.

(5) When the thermal insulation tube or wall is made of a refractory materials such as ceramic and quartz or metal which will not melt even exposed to the molten metal and will not adversely affect the analysis, it serves to retard the solidification of the metal in the entrance chamber. Therefore, shrinkage cavities and distribution of voids in the sample in the sampling chamber may be eliminated.

What is claimed is:

1. An apparatus for determining the carbon contents of molten metal comprising
 (a) a body structure having a sampling container for sampling molten metal, and an open end,
 (b) an entry port formed through said body structure,
 (c) a cover plate adapted to close the open end of said body structure,
 (d) a temperature sensor extended through the center of said cover plate,
 (e) a protective thermal insulation means disposed between said temperature sensor and said entry port for protecting said temperature sensor extended from the cover plate along said temperature sensor in closely spaced apart relationship therewith, whereby said thermal insulation means rapidly cools the molten metal flowing in said sampling container and maintains the molten metal adjacent to said entry port at temperature higher than that in the sampling chamber.

2. An apparatus as set forth in claim 1 wherein, said thermal insulation means is a thermal insulation wall disposed between said temperature sensor and said entry port.

3. An apparatus as set forth in claim 1 wherein, said thermal insulation means is a thermal insulation tube surrounding said temperature sensor.

4. An apparatus as set forth in claim 3 wherein, an air passage is formed in said cover plate between said temperature sensor and said thermal insulation tube.

5. An apparatus as set forth in claim 1 wherein, said thermal insulation means is made of a refractory material such as ceramic and quartz.

6. An apparatus as set forth in claim 1 wherein, said thermal insulation means is made of a metal which is not melted by said molten metal.

7. An apparatus as set forth in claim 3 wherein, an open end of said thermal insulation tube is closed by a plug and an air passage is opened in the side wall of the thermal insulation tube.

8. An apparatus for determining the carbon contents of molten metal comprising
  (a) a body structure having a cylindrical wall structure and a sampling container for sampling molten metal, and an open end,
  (b) a ring-shaped disk disposed between said cylindrical wall structure and said sampling container,
  (c) an entry port formed through said cylindrical wall structure,
  (d) a cover plate adapted to close the open end of said cylindrical wall structure,
  (e) a temperature sensor extended through the center of said cover plate,
  (f) a thermal insulation means for protecting said temperature sensor extended from the cover plate along said temperature sensor in closely spaced apart relationship therewith, whereby said thermal insulation means rapidly cools the molten metal flowing in said sampling container and maintains the molten metal adjacent to said entry port at temperature higher that in the sampling chamber.

9. An apparatus as set forth in claim 8 wherein, said thermal insulation means is a thermal insulation wall disposed between said temperature sensor and said entry port.

10. An apparatus as set forth in claim 8 wherein, said thermal insulation means is a thermal insulation tube surrounding said temperature sensor.

11. An apparatus as set forth in claim 10 wherein, an air passage is formed in said cover plate between said temperature sensor and said thermal insulation tube.

12. An apparatus as set forth in claim 8 wherein, said thermal insulation means is made of a refractory material such as ceramic and quartz.

13. An apparatus as set forth in claim 8 wherein, said thermal insulation means is made of a metal which is not melted by said molten metal.

14. An apparatus as set forth in claim 10 wherein, an open end of said thermal insulation tube is closed by a plug and an air passage is opened in the side wall of the thermal insulation tube.

* * * * *

UNITED STATES PATENT AND TRADEMARK OFFICE
CERTIFICATE OF CORRECTION

PATENT NO. : 4,261,202
DATED : April 14, 1981
INVENTOR(S) : Taizo Kawamoto, et al It is certified that error appears in the above—identified patent and that said Letters Patent is hereby corrected as shown below:

Column 6, line 35: "in" should read --at-- and "high" should read --higher--.

Signed and Sealed this

First Day of December 1981

[SEAL]

Attest:

GERALD J. MOSSINGHOFF

Attesting Officer    Commissioner of Patents and Trademarks